US006820503B2

(12) United States Patent
Sueyoshi et al.

(10) Patent No.: US 6,820,503 B2
(45) Date of Patent: Nov. 23, 2004

(54) HIGH-SPEED ROTATION TESTING APPARATUS

(75) Inventors: Masanori Sueyoshi, Chiba (JP); Akira Tezuka, Chiba (JP); Koji Shibasaki, Chiba (JP); Xinsheng Huang, Ibaraki (JP); Toyotaka Osakabe, Ibaraki (JP); Masao Ono, Kumamoto (JP); Tsutomu Mashimo, 21-45, Takahira 3-chome, Kumamoto-shi, Kumamoto (JP)

(73) Assignees: Tsutomu Mashimo, Kumamoto (JP); Maruwa Electronic Inc., Chiba (JP)

( * ) Notice: Subject to any disclaimer, the term of this patent is extended or adjusted under 35 U.S.C. 154(b) by 0 days.

(21) Appl. No.: 10/237,778

(22) Filed: Sep. 10, 2002

(65) Prior Publication Data
US 2003/0062304 A1 Apr. 3, 2003

(30) Foreign Application Priority Data
Sep. 28, 2001 (JP) ........................... 2001-301480

(51) Int. Cl.[7] ............................................. G01L 3/00
(52) U.S. Cl. ................................................. 73/862.08
(58) Field of Search ........................... 347/57; 73/781, 73/862.08, 761; 439/23; 310/90; 242/573.9

(56) References Cited

U.S. PATENT DOCUMENTS

| 4,095,855 A | * | 6/1978 | Fox ............................ 308/9 |
| 5,325,004 A | * | 6/1994 | Mori et al. ............... 310/67 R |
| 5,537,864 A | * | 7/1996 | Sood ........................... 73/116 |
| 6,176,618 B1 | * | 1/2001 | Kawawada et al. ......... 384/107 |
| 6,400,052 B1 | * | 6/2002 | Suzuki et al. ................ 310/90 |
| 6,615,670 B2 | * | 9/2003 | Shibasaki et al. ............. 73/781 |

FOREIGN PATENT DOCUMENTS

JP        11326130        11/1999

OTHER PUBLICATIONS

English Language Abstract of JP 11–326130.

* cited by examiner

Primary Examiner—Edward Lefkowitz
Assistant Examiner—Octavia Davis
(74) Attorney, Agent, or Firm—Greenblum & Bernstein, P.L.C.

(57) ABSTRACT

An object of the present invention is to achieve more high-speed rotation of a rotor to which a test object is stored, extending the duration of high-speed rotation, and temperature control of a rotor at the time of high-speed rotation. A high-speed rotation testing apparatus of the present invention comprises: a rotor having a hollow for a test object, to which a predetermined test object is stored; a spindle connected to the rotor; a torque applying device for applying a predetermined torque to the spindle, and a casing for sealing the rotor. The casing comprises a decompressing device and a holder for holding the spindle. The holder has a bushing for supporting the spindle and a bushing supporting member for supporting the bushing by inserting thereto. By forming the inner diameter of at least one of the bushing supporting member larger than the outer diameter of the bushing, the bushing supporting member supports the bushing to be rotatable.

16 Claims, 10 Drawing Sheets

HIGH-SPEED ROTATION TESTING APPARATUS

BACKGROUND OF THE INVENTION

1. Field of the Invention

The present invention relates to a high-speed rotation testing apparatus, and in particular, to a high-speed rotation testing apparatus preferably used to achieve processing of test objects stored in the rotor in a high gravitational acceleration field using centrifugal force generated by rotating a rotor at high speed.

2. Description of the Related Art

Conventionally, apparatuses have been under development for enabling generation of an extremely large gravitational acceleration field so as to achieve, by an external force, highly condensed sedimentation diffusion of atoms or molecules of condensed substances formed of two or more elements. A high-speed rotation testing apparatus as shown in FIG. 9 is known to those skilled in the art, and is used for generating a high gravitational acceleration field using centrifugal force by rotating a rotor at high speed. The apparatus will be described.

As shown in FIG. 9, the apparatus comprises a combustor (not shown), an air turbine motor 101 and a rotor 102 for storing a test object container. Combustion gas from the combustor is introduced to the air turbine motor 101 as represented by an arrow A in FIG. 9, and the rotation torque is applied to a rotor shaft 103. The rotor shaft 103 is supported by an oil float bearing 104 and a stator bushing 105. The rotor 102 is secured to the tip of the rotor shaft 103.

Next, the shape of the rotor 102 will be described by referring to FIG. 10. FIG. 10A shows a fragmentary sectional view of the rotor 102 as viewed from the front while FIG. 10B shows the view from the bottom. The rotor 102 has a shape of a cone with the tip being cut off, that is, a substantial conic trapezoid. A shaft hole 102a is formed in the rotor 102 so that the rotor shaft 103 is inserted into the center of the circle, the end faces of the rotor 102. By inserting the rotor shaft 103 to the shaft hole 102a and securing a nut 106 to the tip of the rotor shaft 103, the rotor 102 is interposed between the nut 106 and the stator bushing 105 thereby to be fixed to the tip of the rotor shaft 103. Also, on one end face of the rotor 102, that is, the face of the rotor shaft 103 on the tip side, hollows 107a and 107b for test objects with a predetermined depth are formed along a ridgeline arranged towards the other end face (air turbine motor side). A condensed substance M as the test object is stored in the hollows 107a and 107b and then the rotor 102 is rotated at high speed. Thereby, the test object can be processed under large gravitational acceleration by the centrifugal force.

Specifically, with the high-speed rotation testing apparatus, an acceleration field more than 200,000 gravitation acceleration (in the followings, referred to as "g") can be generated at the temperatures over 60° C. In general, the acceleration field $\alpha$ is represented by $\alpha = r\omega^2$ provided that the angular velocity around the rotor shaft is $\omega$, and the length of the perpendicular from an object to the rotor shaft is r. The required rotating speed varies according to the size of the inner radius r of the test object container. For example, in the case where the inner radius r of the test object container is 20 mm, it is necessary to achieve high-speed rotation with the maximum rotating speed of 200,000 rpm or more in order to generate 810,000 g of gravitational acceleration.

However, there are problems as described below with the high-speed rotation testing apparatus in the example of the related art.

First, there is a shaft hole provided in the rotational center of the above-described rotor. Thus, the shaft hole cannot endure the stress at the time of high-speed rotation due to a high-gravitational acceleration field, which may result in deformation or the like of the rotor. Therefore, it is necessary to limit the rotating speed of the rotor to a predetermined value.

Also, the atmosphere surrounding the rotor is in the atmospheric air so that there is a frictional resistance generated by windage, which leads to a problem that the rotating speed is suppressed by the resistance. If the frictional resistance by windage is suppressed through decompressing the atmosphere surrounding the rotor, the resistance on the rotor is reduced so that the rotating speed can be increased. However, in this case, heat transfer via the air cannot be utilized so that the heating/cooling efficiency of the rotor is deteriorated. Therefore, it is difficult to control the temperature of the test object and the test contents of the test object are to be limited.

Further, by supporting the rotation shaft by the stator bushing, the relative speed of the rotation shaft and the bushing is increased, thereby causing seizure due to the friction generated therebetween. Hence, it is difficult to continue high-speed rotation of the rotor for a long time.

SUMMARY OF THE INVENTION

The present invention has been designed to overcome the foregoing problems. Specifically, an object of the invention is to provide a high-speed rotation testing apparatus which can achieve more high-speed rotation of a rotor to which a test object is stored and can extend the duration of high-speed rotation while enabling the control of the temperature of the rotor at the time of high-speed rotation.

A high-speed rotation testing apparatus according to present invention, comprising: a rotor having a hollow for a test object for storing a predetermined test object; a spindle whose one end portion is connected to a rotation center of said rotor; a torque applying device connected to the other end portion of said spindle for applying a predetermined torque to said spindle; and a casing for storing said rotor by sealing, wherein said casing comprises a decompressing device for decompressing atmospheric pressure inside said casing and a holder for holding said spindle by inserting through said spindle, wherein said holder comprises at least one bushing for supporting said spindle and a bushing supporting member for supporting said bushing by inserting therethrough, wherein an inner diameter of said at least one bushing supporting member is formed larger than an outer diameter of said bushing to be inserted into said bushing supporting member so that said bushing supporting member supports said bushing to be rotatable.

With the configuration, torque applied from the torque applying device to the spindle transmits to the rotor so that the rotor rotates at a high speed under decompressed atmosphere. At this time, the spindle is supported by the bushing provided inside the supporting means. Thus, due to the friction between the spindle and the bushing, torque is applied so that the bushing is also rotated in the same direction as the rotating direction of the spindle. The bushing is supported by a bushing supporting member with a predetermined clearance in between so that the bushing is rotatable against the bushing supporting member. Hence, when the bushing is fixed to the bushing supporting member, the relative rotating speeds of the bushing and the bushing supporting member is suppressed. Thus, the friction generated between the members can be reduced thereby preventing generation of seizure. As a result, more high-speed rotation of the rotor can be achieved and, at the same time, it becomes possible to maintain high-speed rotation for a long time.

And said bushing which is rotatably supported by said predetermined bushing supporting member may be provided only on said torque applying device side of said holder. In other words, the bushing provided in the spindle on the rotor side may be supported by being fixed to the bushing supporting member. Thereby, the spindle is stably supported near the rotor. Thus, swing of the spindle can be suppressed and stable high-speed rotation of the rotor can be achieved. At the same time, friction generated between the spindle and the bushing can be suppressed on the torque applying device side. Therefore, high-speed rotation of the rotor can be achieved for a long time as in the case described earlier.

Moreover, in a rotation center of said rotor, it is preferably a spindle connecting portion projected from said rotor towards said torque applying device side is formed for connecting to said spindle. And, in the projected end of said spindle connecting portion, a shaft hole for inserting and connecting said spindle is formed while providing a depth of the shaft hole not to be inserted into said spindle connecting portion.

Thereby, the spindle connecting portion for connecting the spindle is formed being projected from the rotational center of the rotor. In other words, the spindle connecting portion is formed as one body with the rotor. Since the spindle is connected by inserting into the shaft hole formed in a predetermined depth from the projection end of the spindle connecting portion, it becomes unnecessary to form a shaft hole in the rotational center of the rotor inserting through the spindle connecting portion and the rotor main body. Therefore, such a problem including deformation of the shape of the rotor or the like due to unbearable stress of the centrifugal force by the high-speed rotation imposed on the through-hole can be suppressed, which may otherwise occur in the case with a through-hole in the rotor as a shaft hole. In other words, the state of the rotor such as the shape of the rotor at the time of high-speed rotation can be stabilized so that more high-speed rotation can be achieved.

Conventionally, an air turbine driven by combustion gas is used as a torque applying device. However, it is preferably the torque applying device is an air turbine which is rotationally driven by a supply of compressed air or an electric driving motor. Thereby, it becomes unnecessary to use a combustor which generates a combustion gas. Thus, unlike the related art, transmission of the heat from the combustor to the test object stored in the rotor can be avoided. As a result, increase in the temperature of the rotor at the time of high-speed rotation, that is, increase in the temperature of the test object can be prevented. Hence, the temperature control of the test object can be achieved.

Moreover, in the vicinity of said rotor inside said casing, a radiation member with a predetermined area is provided and, at the same time, a radiation temperature controller for controlling temperatures of said radiation member is provided. It is more preferably said radiation member is formed in annular shape so as to surround a rotation periphery of said rotor. By heating/cooling the radiation member using the temperature controller, radiation heat is generated in the rotor by the radiation from the radiation member. Thereby, the rotor can be heated or cooled. At this time, the rotor can be effectively heated/cooled by providing the radiation member in an annular form to surround the rotor. Thereby, even if the rotor is in the decompressed atmosphere, the temperature of the rotor can be controlled so that the processing temperature of the test object can be set.

BRIEF DESCRIPTION OF THE DRAWINGS

FIG. 2 is an illustration showing the rotor shown in FIG. 1, in which

FIG. 10 is an illustration showing the shape of a rotor according to the related art, in which FIG. 10A shows a fragmentary sectional view of the rotor viewed from the front while

DETAILED DESCRIPTION OF THE PREFERRED EMBODIMENTS (First Embodiment)

Figure 1:
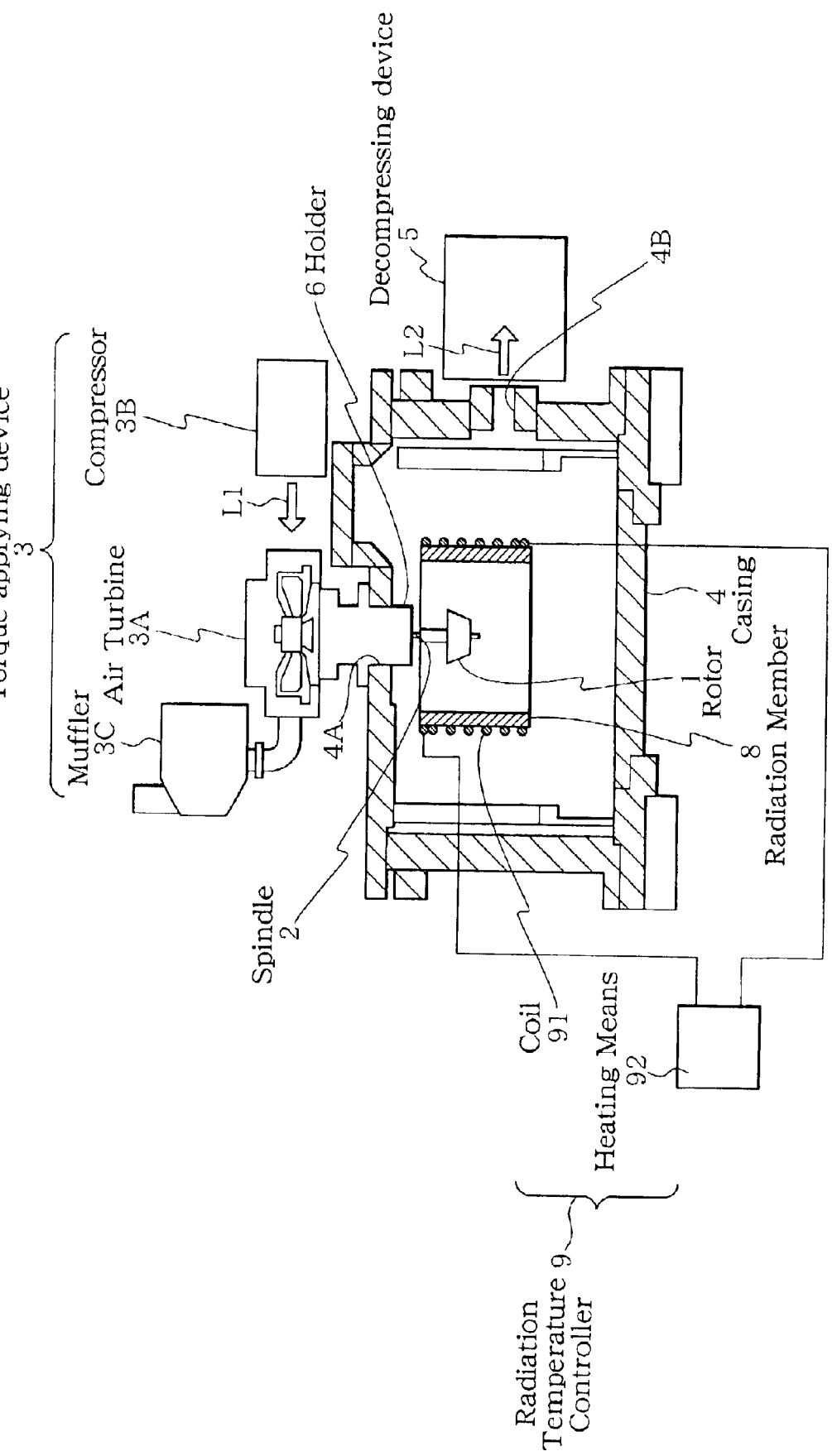
FIG. 1 is a cross section showing the outline of the configuration according to a first embodiment of the present invention.
Figure 2A:
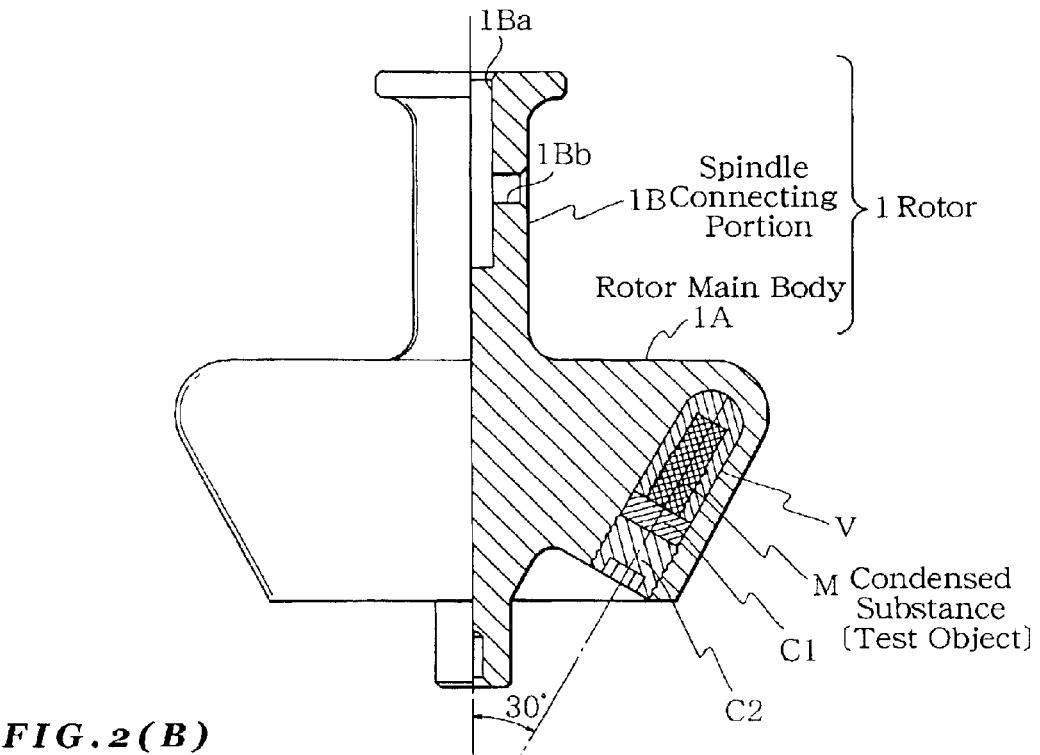
FIG. 2A shows a fragmentary sectional view of the rotor viewed from the front and FIG. 2B shows the view of the rotor from the bottom.
Figure 2B:
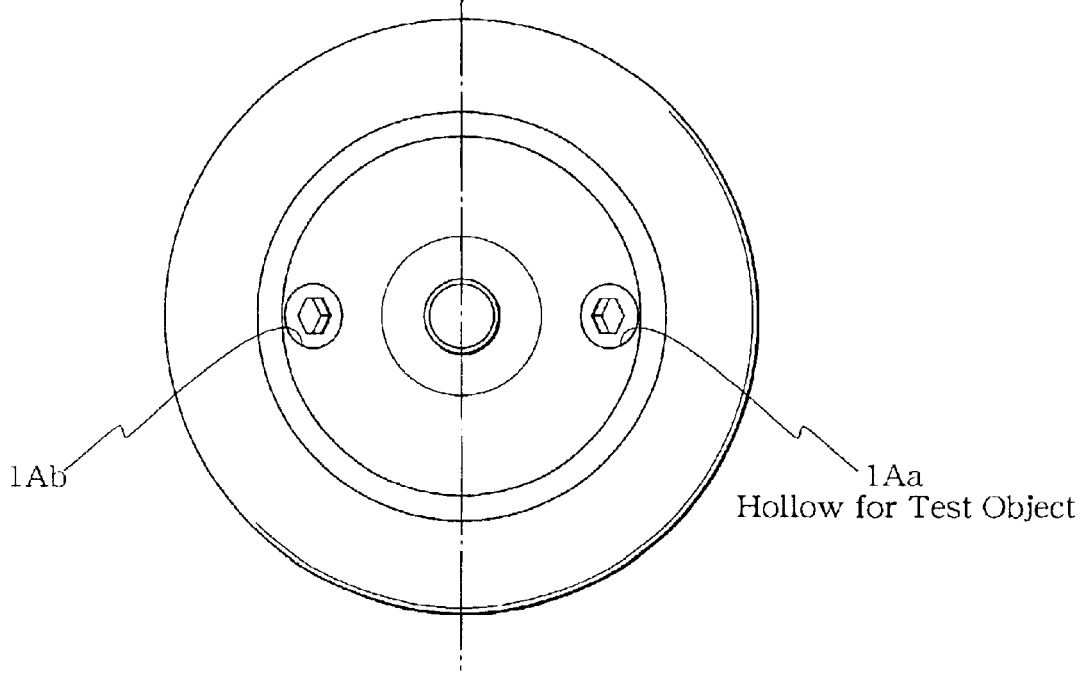
Figure 3:
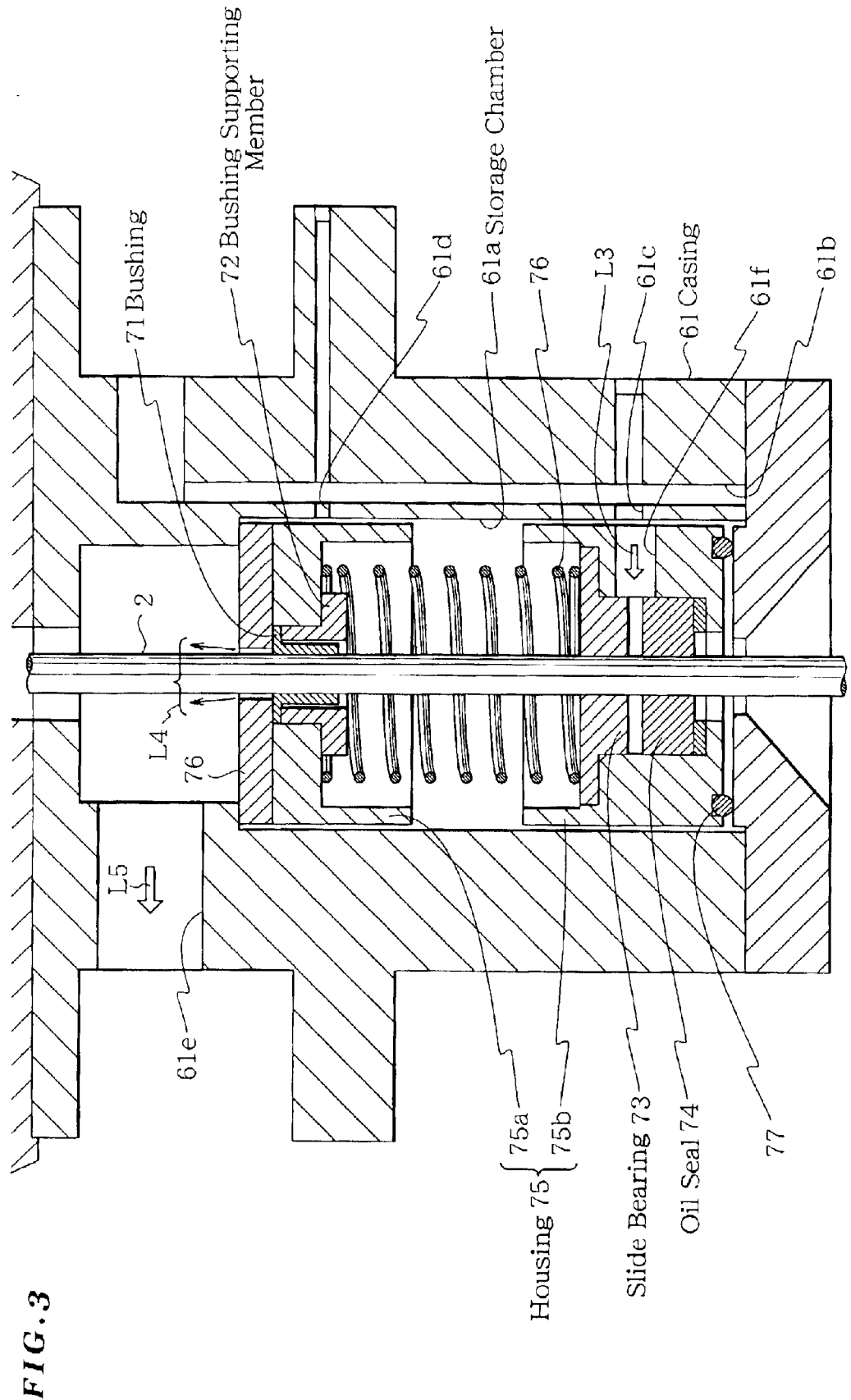
FIG. 3 is a cross section showing the configuration of a holder shown in FIG. 1.

In the followings, a first embodiment of the present invention will be described by referring to FIG. 1 to FIG. 7. FIG. 1 is a schematic cross-sectional view showing the configuration of the present invention. FIG. 2 is an illustration for describing the shape of a rotor and FIG. 3 is a cross section showing the configuration of a holder. FIG. 4 to FIG. 7 are figures showing the results of high-speed rotation test carried out by using the apparatus.

(Overall Configuration)

As shown in FIG. 1, the high-speed rotation testing apparatus according to the first embodiment comprises: a rotor 1 having a hollow for a test object for storing a predetermined test object; a spindle 2 whose one end is connected to the rotational center of the rotor 1; a torque applying device 3 for applying a predetermined torque to the spindle 2 by being connected to the other end of the spindle 2; and a casing 4 for sealing and storing the rotor 1. Further, the casing 4 comprises a decompressing device 5 for decompressing the atmospheric pressure inside the casing 4 and a holder 6 for holding the spindle 2 by inserting into the spindle 2. Torque from the torque applying device 3 is transmitted via the spindle 2 to the rotor 1 which, as in FIG. 1, hangs from the spindle 2. Thereby, high-speed rotation of the rotor 1 can be achieved. Detailed description will be provided hereinafter.

(Rotor)

The rotor 1 will be described by referring to FIG. 2. FIG. 2A is a fragmentary sectional view of the rotor 1 viewed from the front. FIG. 2B is a view of the rotor 1 shown in FIG. 2A viewed from the bottom.

The rotor 1 is, as will be described later, a rotor which is rotated by the torque from the torque applying device 3 being transmitted via the spindle 2. The rotor 1 is composed of a substantially conic trapezoid rotor main body 1A and a spindle connecting portion 1B which is positioned in the rotational center of the main body 1A and projects towards the rotor shaft direction. The rotor 1 is not formed by combining the rotor main body 1A and the spindle connecting portion 1B but formed as one body. Therefore, it is desirable that the rotor 1 be fabricated by scraping the cast bulk material. However, it is not limited to this fabricating method but may be fabricated by an article of cast metal. By forming the two portions as one body as described, the strength of the rotor itself can be improved to the extent which can endure the centrifugal force by the high-speed rotation. Here, for convenience' sake, the rotor main body 1A and the spindle connecting portion 1B will be described separately for describing the rotor 1.

The rotor main body 1A is a substantial cone as described. In other words, it is a shape which is obtained by cutting a cone at a predetermined height from the bottom face by a surface parallel to the bottom face, and then cutting the tip portion side. It is arranged with the cut side facing the downward direction of the apparatus. In other words, the bottom face of the original conic shape is positioned to be the upper portion side and the cut portion is positioned to be the lower portion side. The surface on the lower portion side is, needless to say, in an annular shape, and it is uniformly concaved from its circumference to the center (see cross section in FIG. 2A). However, the center portion is projected towards the axial direction. Therefore, an annular shape concave is formed in the surface on the lower portion side.

In the concave, hollows 1A$a$ and 1A$b$ for test object are formed extending towards the upper direction of the apparatus along the ridgeline of the cone. The two hollows 1A$a$ and 1A$b$ for the test object have a predetermined depth and are formed in bilateral symmetry (see FIG. 2B). However, the numbers are not limited to two to be provided.

The hollows 1A$a$ and 1A$b$ for test object are hollows for storing a test object M which is a condensed substance with which a rotation test is carried out. In the hollows 1A$a$ and 1A$b$, a test object container (capsule) V to which the test object M is stuffed and a predetermined stopper C1 is thrust is inserted. Then, the hollows 1A$a$ and 1A$b$ are closed by another stopper C2. Also, the hollows 1A$a$ and 1A$b$ are formed to slope against the rotor shaft at an angle of about 30° (see FIG. 2A), however, it is not limited to this.

Furthermore, as described, a large gravitational acceleration is generated in the rotor 1. Also, the object of the apparatus is not only to give a centrifugal force to the test object but to induce diffusion and phase change reaction. Thus, it is necessary to apply heat. Therefore, it is desirable that the rotor 1 has high strength and is formed with a material with an excellent heat-resistance. Therefore, the embodiment uses the rotor 1 formed with a titanium alloy (Ti-6A1-4V). However, the material for the rotor 1 is not limited to this. For high temperatures, iron-nickel alloy (Inconel 718) or ceramics may also be used. Also, as will be described later, when cooling the rotor 1, the rotor 1 formed with other material may be used.

The spindle connecting portion 1B is a substantial column shape member provided on the upper side of the rotor main body 1A. The column member is positioned in such manner that the central axis of the column and the rotor shaft of the rotor main body 1A are to be in the same straight line. In the upper end portion of the spindle connecting portion 1B, that is, in the projection end projected from the rotor main body 1A, a shaft hole 1B$a$ to which the spindle 2 is inserted to be connected is formed on the rotor shaft of the rotor 1. The shaft hole 1B$a$ is formed towards the downward direction and has a predetermined depth not to insert into the spindle connecting portion 1B. Thus, needless to say, the shaft hole 1B$a$ does not reach the rotor main body 1A.

Also, a tapped hole 1B$b$ which inserts vertically to the shaft hole 1B$a$ from outside the spindle connecting portion 1B is formed. By inserting the spindle 2 to the shaft hole 1B$a$ and tightening the screw from the tapped hole 1B$b$, the spindle 2 can be connected to the spindle connecting portion 1B. Thereby, torque from the torque applying device 3 can be transmitted to the rotor 1.

In the example of the related art, a through-hole is formed in the center of the rotor 1, and the spindle 2 is inserted to the through-hole. Then, the rotor 1 is connected to the tip of the spindle 2 by nut or the like. However, in the case, the through-hole cannot endure the stress of the centrifugal force by the high-speed rotation which leads to a problem that the shape of the rotor itself is deformed. In the embodiment, such disadvantage can be improved. Therefore, it is possible to provide a strong rotor and more high-speed rotation or extension of the duration of the high-speed rotation can be achieved.

(Spindle)

One end of the spindle 2 is, as described, connected to the spindle connecting portion 1B of the rotor 1 and the other end is connected to the torque applying device 3. Also, the center portion is supported by a holder 6 to be described later. Thereby, torque is transmitted to the rotor 1 and, at the same time, a stable high-speed rotation of the rotor 1 can be achieved.

(Torque Applying Device)

The torque applying device 3 is composed of an air turbine 3A which is rotationally driven through receiving a supply of compressed air, a compressor 3B for supplying the compressed air, and a muffler 3C for discharging air introduced to the air turbine 3A. The air turbine 3A, as shown in FIG. 1, introduces the air compressed by the compressor 3B from the right-hand side direction (an arrow L1) of the air turbine 3A, and comprises on the inside a rotary vane (not shown) rotated by the wind pressure by the introduced air. The rotational center of the rotary vane is really the drive shaft (no shown) of the air turbine 3A itself. In other words, the rotary vane is provided at a predetermined position of the drive shaft. The drive shaft is connected to the above-mentioned other end of the spindle 2 so as to transmit the driving force to the spindle 2.

Although not shown in the figure, the rotary vane has a dual structure and each vane is provided in the opposite direction from each other. Further, in order to be able to supply the compressed air to each rotary vane, a partition is provided between each vane. Thus, the rotor 1 can be rotated at a high speed by supplying the compressed air to the one of the rotary vane. However, at this time, if the compressed air is supplied to the other rotary vane, the other rotary vane rotates to the opposite direction. Thereby, the rotational speed of the rotor 1 can be decreased. Hence, by providing two rotary vanes as described and, at the same time, switching the introduction of the compressed air, the rotational speed of the rotor 1 can be controlled with high precision. As described above, a switch controller (not shown) is provided in the air turbine 3A for switching the compressed air from the compressor 3B to be induced to either one of the rotary vanes.

The muffler 3C absorbs the noise of the air discharged from the air turbine 3A and discharges the air. The functions of the air turbine 3A, the compressor 3B and the muffler 3C are the same as those used in general so that the description will be omitted.

In the example of the related art, an air turbine driven by combustion gas is used as the torque applying device 3. In other words, by using a turbo charger which is driven by using combustion gas from a jet-engine combustor, it makes it possible to achieve high-speed rotation in a short time. However, in this case, it is difficult to control the most important element for carrying out a test, that is, the number of revolutions and, at the same time, the heat from the combustion gas is transmitted to the rotor 1. Therefore, there causes various problems. On the contrary, in the present invention, an air turbine by the compressed air is used. Thus, it becomes easy to control the number of revolutions of the driving source and, at the same time, generation of heat can be suppressed when driving. As a result, the number of revolutions and the temperature of the rotor 1 can be easily set so that tests can be carried out under various conditions. Thereby, convenience for the users can be improved. Accordingly, the torque applying device 3 may be any thing as long as it can suppress generation of heat at the time of driving. For example, an electric driving motor may be used. In this case, the number of revolutions of the driving source can be also controlled with high precision. Therefore, it becomes easy to control the number of revolutions of the rotor 1.

(Casing)

The casing 4 is a casing with a predetermined thickness for storing the rotor 1 in a predetermined atmosphere. The casing 4 has a substantial rectangular shape and the inside space takes the same shape. Specifically, it is composed of plate members forming each wall and seal (not shown) is applied to the connection. As will be described later, the inside space of the casing 4 is a sealed space.

On the upper portion of the casing 4, a hole 4A for holder is formed so as to position a holder 6 to be described later for supporting the spindle 2. The holder 6 is fitted into the hole 4A and outer periphery of the hole 4A is sealed. Thereby, the tip of the spindle supported by the holder 6 is inserted to the inside of the casing 4 and, by connecting the rotor 1 to the tip, the rotor 1 can be stored inside the casing 4.

Also, a discharge port 4B is formed on the side face of the casing 4. The discharge port 4B is normally closed. However, it is also possible to provide a decompressing device 5 such as a vacuum pump on the tip. In this case, by discharging the air from the inside space of the casing 4 to the outside using the pump (see an arrow L2 in FIG. 1), it is possible to provide the inside state of the casing 4 to be a vacuum or close to a vacuum. For example, provided the atmospheric pressure is $10^5$ Pa, it can be made $10^2$ Pa or less by decompression. Thereby, the atmosphere surrounding the rotor 1 becomes a decompressed state and friction resistance by the rotor 1 and air can be decreased. As a result, losses due to the friction at the time of high-speed rotation of the rotor 1 can be suppressed. Therefore, a burden on the torque applying device 3 can be suppressed so that more high-speed rotation can be achieved. Accordingly, torque necessary for maintaining the rotation speed of the rotor 1 can be suppressed and high-speed rotation can be maintained for a long time.

Furthermore, the casing has a function of collecting the pieces of the rotor 1 in the case where the rotor 1 is broken down and scattered in a high-speed rotation teat. Accordingly, the walls of the casing 4 are designed to have strength sufficient to endure the impact of collision by the broken pieces.

(Holder)

The holder 6 is a mechanism functioning as a bearing for supporting the spindle 2 in the center portion by inserting therethrough. The holder 6 is, as described, provided by fitted into the upper wall of the casing 4. The holder 6 will be described below by referring to FIG. 3. FIG. 3 is a cross section showing the configuration of the holder 6.

As shown in FIG. 3, the holder 6 has a cylindrical shape and the spindle 2 inserts into the center. The holder 6 comprises a casing 61 for forming the cylindrical shape. The casing 61 has a predetermined space inside and the space is formed as a storage chamber 61a to which various parts are stored. A predetermined part for supporting the spindle 2 is stored in the storage chamber 61a and the inside is always filled with a lubricant. Thus, inside the casing 61, specifically, on the walls for forming the storage chamber 61a, a lubricant chamber 61b capable of supplying a lubricant from outside is provided adjacent to the storage chamber 61a and two supply ports 61c and 61d are provided for supplying a lubricant from the lubricant chamber 61b to the storage chamber 61a. Also, a discharge port 61e capable of discharging the lubricant from the inside of the storage chamber 61a to the outside is provided in the casing 61. Therefore, when using the apparatus, it is possible to circulate the lubricant so as to always fill inside the storage chamber 61a.

Also, in the storage chamber 61a, a bushing 71 for supporting the spindle 2 in the upper portion and a bushing supporting member 72 for supporting the bushing 71 by inserting therethrough are provided. Also, in the lower portion of the spindle 2, provided are a slide bearing 73 for supporting the spindle 2 and a an oil seal 74 for sealing so that the lubricant filling inside the storage chamber 61a does not leak to the lower portion of the casing 61. Furthermore, a housing 75 for supporting the bushing supporting member 72, the slide bearing 73, the oil seal 74 and the like is also provided.

The housing 75 is composed of a top cylindrical body 75a positioned in the upper portion and a bottom cylindrical body 75b positioned in the lower portion. A thrust spring 76 is inserted between the cylindrical bodies 75a and 75b arranged towards the vertical direction so as to separate the cylindrical bodies 75a and 75b.

The top cylindrical body 75a has a cylindrical shape with a roof plate on the top and a through-hole is provided in the center of the roof plate to which the bushing supporting member 72 is fitted. The inner diameter of the through-hole is substantially the same as the outer diameter of the bushing supporting member 72 so that the bushing supporting member 72 can be fixedly supported. Further, a washer 76 is mounted on the top of the top cylindrical body 75a. As will be described later, the bushing 71 is loosely inserted to the bushing supporting member 72.

The top cylindrical body 75a has a cylindrical shape with a bottom plate on the bottom and a through-hole is provided in the center of the bottom plate to which the spindle 2 is loosely inserted. Also, a concave portion to witch the oil seal 74 with larger diameter than that of the through-hole is fitted is provided in the upper portion than the bottom plate. Also, in the further upper portion, a concave portion to which the slide bearing 73 is fitted is provided in the same manner. The oil seal 74 and the slide bearing 73 are fitted thereto by being fixed to the bottom cylindrical body 75b. The bottom cylindrical body 75b is arranged inside a storage chamber 45 with its bottom plate being substantially abutted against the lower inner wall surface of the storage chamber 61a.

Also, in the peripheral walls of the bottom cylindrical body 75b, a through-hole 61f for supplying a lubricant to the inside is provided. The through-hole 61f is provided in the position corresponding to the above-described supply port 61c for supplying the lubricant to the inside of the storage chamber 61a. The lubricant is supplied in the direction of an arrow L3 shown in FIG. 3.

The roof plate of the top cylindrical body 75a is pressed in the upper inner wall surface direction of the storage chamber 61a via the thrust spring 76. On the other hand, the bottom plate of the bottom cylindrical body 75b is pressed in the lower inner wall surface direction of the storage chamber 61a. At this time, an O ring 77 is inserted between the bottom plate of the bottom cylindrical body 75b and the lower inner wall surface of the storage chamber 61a thereby to prevent the leakage of the lubricant to the outside, which is present between the periphery of the housing 75 and the inner wall surface of the storage chamber 61a. Also, in the bottom portion of the bottom cylindrical body 75b, as described earlier, the oil seal 74 provided to surround the periphery of the spindle 2 is stored, thereby preventing the lubricant inside the housing 75 from leaking to the lower portion through the spindle 2.

Now, the above-described bushing 71 and the bushing supporting member 72 will be described. The inner diameter of the bushing 71 is substantially the same as the shaft diameter of the spindle 2. However, it is not exactly the same so that there is a minute clearance formed in between when the spindle 2 is inserted to the bushing 71, thereby allowing the lubricant to be inserted therebetween. The lubricant flows from the bottom to the top (see an arrow L4), and is discharged from the discharge port 61e formed on the top of the casing 61 (see an arrow L5). The outer diameter of the bushing 71 only near the tip portion is formed to be larger. However, the outer diameter is smaller than that of the through-hole formed in the center portion of the top cylindrical body 75a.

The bushing supporting member 72 supports the upper end portion of the bushing 71 by hanging it from the upper end portion of the bushing supporting member 72 and support the other outer diameter portion. At this time, the inner diameter of the portion in the bushing supporting member 72 for supporting the bushing 71 is formed larger than the outer diameter of the bushing 71. In other words, the bushing supporting member 72 supports the bushing 71 to be rotatable. Further, needless to say, the lubricant is to be inserted between the bushing supporting member 72 and the bushing 71 so that the relative rotation is to be achieved smoothly. The outer diameter of the bottom end portion of the bushing supporting member 72 is formed to be larger (see FIG. 3).

Thereby, first, by rotating the spindle 2, the lubricant is inserted between the spindle 2 and the bushing 71. However, the amount is very small so that there may be a friction generated. Thereby, torque is generated so as to rotate the bushing 71 in the same direction as the rotating direction of the spindle 2. At this time, there is a predetermined clearance formed between the bushing 71 and the bushing supporting member 72 for supporting it, and the clearance is filled with the lubricant. Therefore, the bushing 71 is also rotated in the same direction as the spindle 2. The friction generated between the bushing 71 and the bushing supporting member 72 is decreased. Hence, by rotating the bushing 71 in the same direction as the rotation of the spindle 2, the relative rotating speed of the spindle 2 and the bushing 71 is suppressed to be slow. Thereby, seizure due to the friction can be avoided.

Furthermore, since there is a predetermined clearance formed between the bushing 71 and the bushing supporting member 72, by the lubricant inserted between the clearance, swing of the spindle 2 can be suppressed and a stable rotation of the spindle 2 can be achieved.

On the contrary, the slide bearing 73 supporting the spindle 2 in the lower portion is a bearing with the inner diameter substantially the same as the outer diameter of the spindle 2. Therefore, it surely supports the spindle 2 in the lower portion so that the swing of the spindle 2, that is, the swing of the rotor 1 can be suppressed. As described, by using the above-described slide bearing for the bearing near the rotor 1, a stable high-speed rotation of the rotor 1 can be achieved.

In the embodiment, the case where the above-described bushing 71 and the bushing supporting member 72 are provided only on the top side of the holder 6 is described as an example. However, it is not limited to this. The bushings 71 and the bushing supporting members 72 may be provided in a plurality of positions. In other words, the bearing near the rotor 1 may be formed by the bushing 71 and the like.

(Radiation Member)

Also, a radiation member 8 with a predetermined area is provided near the rotor 1 inside the casing 4. Specifically, the radiation member 8 is prepared by forming a plate member with a predetermined thickness to a annular shape so as to surround the rotating periphery of the rotor 1 (see FIG. 1). Further, although not shown in FIG. 1, the radiation member 8 is positioned by being hung from the upper portion of the casing 4.

Also, a radiation temperature controller 9 for controlling the temperature of the radiation member 8 is provided in the casing 4. In the embodiment, the radiation temperature controller 9 is for heating the radiation member 8 and is formed with a seed heater. Specifically, a plurality of coils 91 are provided by being abutted against the outer periphery of the radiation member 8 and the coils 91 are connected to a heating means 92 which is an electric source for flowing a predetermined current. Furthermore, the radiation temperature controller 9 comprises a temperature sensor and a computer (not shown) for controlling the amount of electric supply from the electric source so as to control the rotor 1 to be a predetermined temperature by adjusting the temperature of the radiation member 8 while measuring the temperature of the rotor 1.

Also, in the case of heating the rotor 1, it is desirable that the radiation member 8 be made of carbon. Furthermore, when heating the radiation member 8, high-frequency heating may be used other than using joule heating.

As described, by heating the radiation member 8 using the radiation temperature controller 9, radiation heat is generated in the rotor 1 by the radiation ray from the radiation member 8. Thereby, the rotor 1 can be heated. Even in the case where it is difficult to supply calorific value to the rotor 1 by air convection or the like because the periphery of the rotor is decompressed atmosphere, the rotor 1 can be heated and the temperature can be controlled by using the radiation heat as described. Thereby, the test object can be processed at a desired processing temperature.

(Operation)

Next, an operation of the apparatus according to the embodiment will be described. First, before rotating the rotor 1, the atmospheric pressure inside the casing 4 is decompressed to $10^2$ Pa or less by a vacuum pump (decompressing device) 5. Then, the compressor 3B is started to induce the compressed air to the air turbine 3A (an arrow L1 in FIG. 1). Thereby, the air turbine 3A is rotationally driven and torque generated thereby is transmitted to the rotor 1 via the spindle 2. The compressed air which has supplied the rotating force to the air turbine 3A is discharged to the outside via the muffler 3C.

When the spindle 2 is rotated, torque from the spindle 2 is supplied by the friction to the bushing 71 which supports the spindle 2. At this time, a thin film of lubricant is formed between the spindle 2 and the bushing 71. However, friction is also generated in this case so that the rotating force is also supplied to the bushing 71 in the rotating direction of the spindle 2. There is a predetermined clearance formed between the bushing 71 and the bushing supporting member 72 to be filled with the lubricant. Thus, the bushing 71 is rotated in the same rotating direction of the spindle 2. Thereby, the relative rotating speed of the spindle 2 and the bushing 71 is decreased. As a result, the friction between the members is decreased so that seizure can be avoided.

The torque of the spindle 2 is transmitted to the rotor 1 connected to the end portion of the spindle 2 so that the rotor 1 is rotated. The atmosphere surrounding the rotor 1 is decompressed so that there is little air resistance. Thereby, loss at the time of rotation is suppressed and high-speed rotation of the rotor 1 can be achieved.

Also, during or before starting the rotation of the rotor 1, the radiation member 8 is heated by the radiation temperature controller 9. The radiation ray is radiated from the radiation member 8 to the rotor 1 thereby generating the radiation heat in the rotor 1. In the heated rotor 1, the heat is transmitted to the test object stored inside. Thereby, the test object can be set to a predetermined temperature and it can be processed at a predetermined gravitational field.
(Experiment)

Next, a high-speed rotation experiment carried out by using the apparatus according to the embodiment will be described by referring to FIG. 4 to FIG. 7. At this time, a rotor 1 with 70 mm diameter was used.

Figure 4:
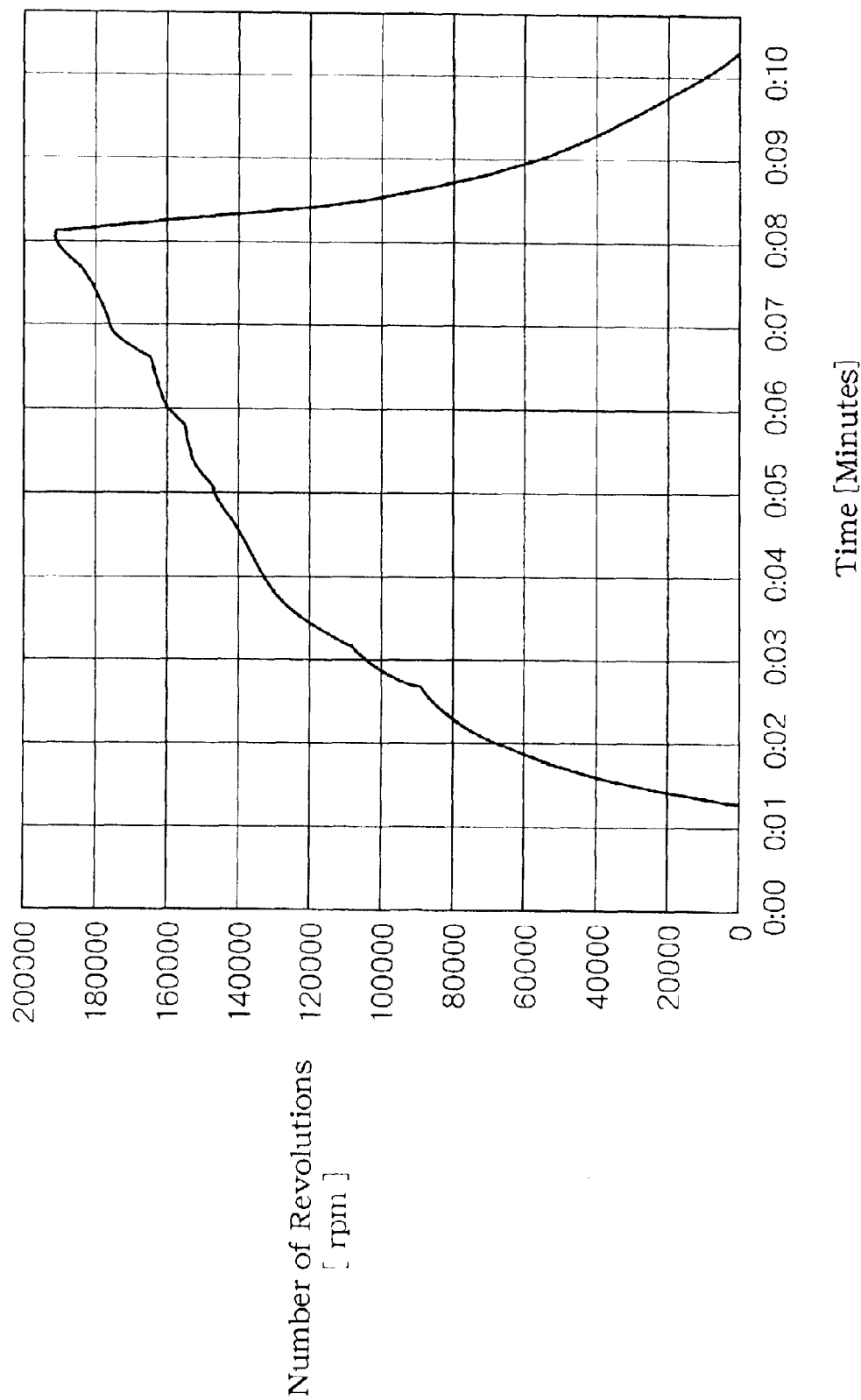
FIG. 4 is a figure showing the result of a high-speed rotation test using an apparatus according to the first embodiment.

FIG. 4 is a figure showing the result of a rotation test using a rotor 1 made of a titanium alloy (Ti-6A1-4V) under a condition where the atmosphere surrounding the rotor 1 was at a normal temperature and decompressed. The horizontal axis represents the time (minutes) and the vertical axis represents the number of revolutions (rpm) As can be seen from the figure, the number of revolution of the rotor 1 reaches 190,000 rpm after 8 minutes from the start thereby achieving a high-speed rotation. At this time, the gravitational acceleration imposed on the condensed substance M as the test object is 1,110,136 g at the maximum diameter. Therefore, with the apparatus, a high-speed rotation of the rotor 1 can be achieved and the test object can be processed in a high gravitational acceleration field over 1,000,000 g.

Figure 5:
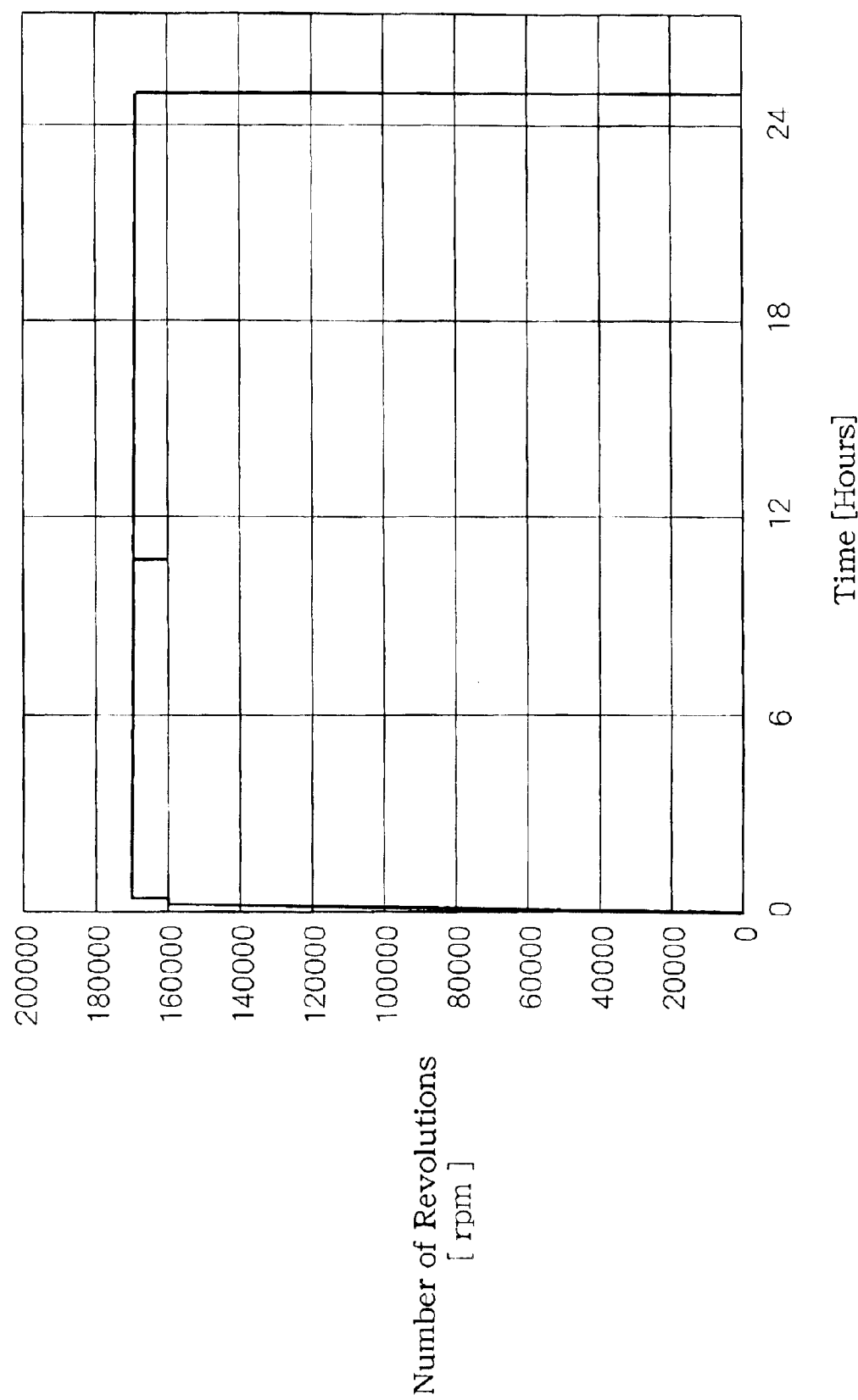
FIG. 5 is a figure showing the result of a continuous rotation test using the apparatus according to the first embodiment.

FIG. 5 is a figure showing the result of a test in which the rotor 1 is continuously rotated at 170,000 rpm for 24 hours under the same condition described above. The horizontal axis represents time (hours) and the vertical axis represents the number of revolutions (rpm). As can be seen from the figure, it is clear that the number of revolutions can be maintained substantially at 170,000 rpm for 24 hours. Thus, even in the case where a high-speed rotation is maintained for a long time, the number of revolutions can be stably maintained. The high gravitational acceleration field at the maximum diameter of the test object was 888,724 g at this time. Therefore, the apparatus can maintain the generation of high gravitational field for a long time so that it is also considered to have an excellent durability.

Figure 6:
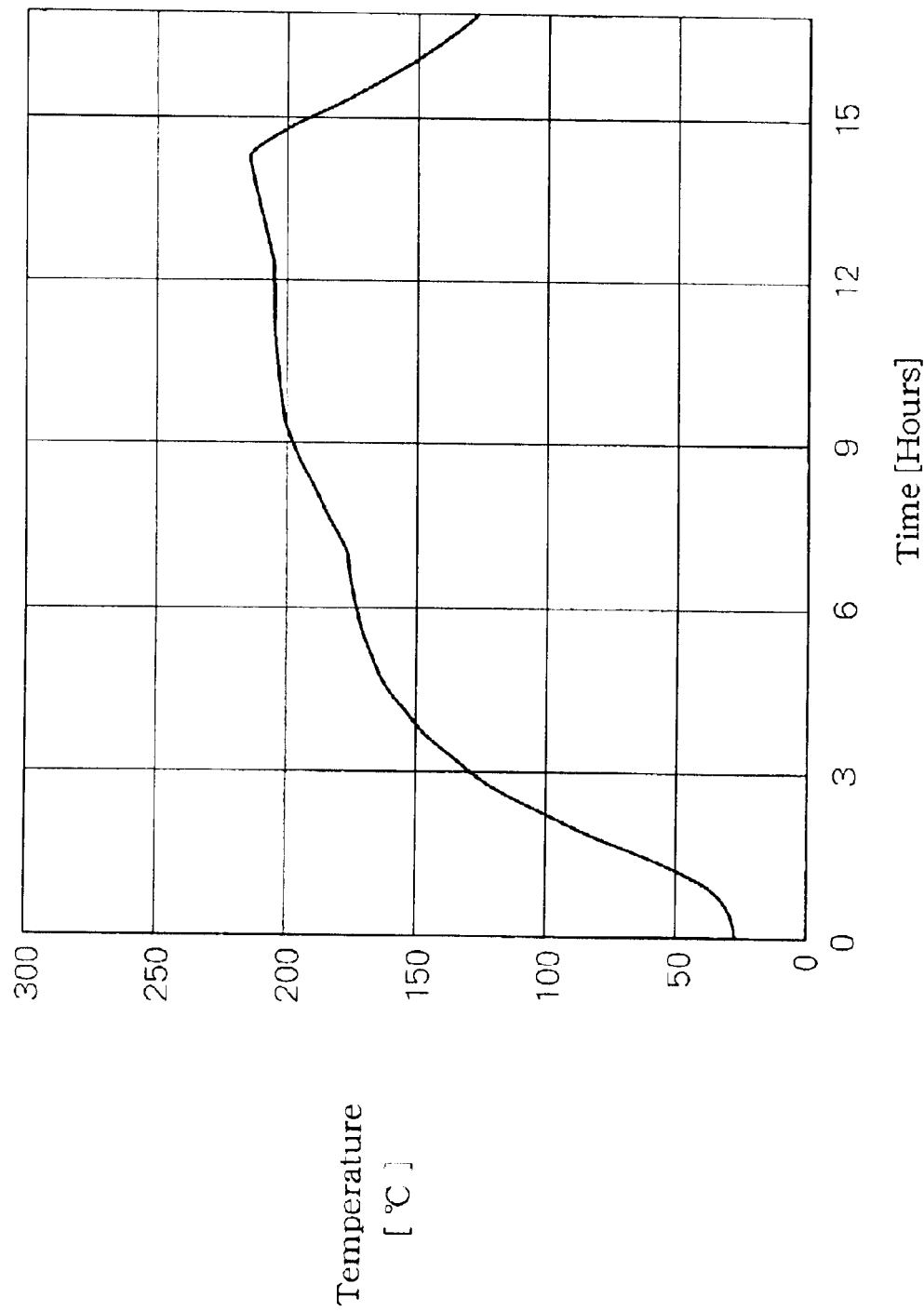
FIG. 6 is a figure showing the result of a heating test of a rotor using the apparatus according to the first embodiment.

FIG. 6 is a figure showing the result of a test in which the rotor 1 made of iron-nickel alloy (Inconel718) was heated under the condition where the atmosphere surrounding the rotor 1 was at 200° C. and decompressed. The horizontal axis represents the time (hours) and the vertical axis represents the temperature (° C.). At this time, the rotor 1 was at standstill and a thermocouple was attached to the rotor 1. The temperature of the rotor 1 was measured thereby. As can be seen from the figure, the temperature of the rotor 1 reaches 200° C. after 9 minutes from the start. Accordingly, it is clear that the rotor 1 can be heated by the radiation heat. Therefore, even in the case where the rotor 1 is rotated under the decompressed condition, the temperature of the rotor 1 can be controlled.

Figure 7:
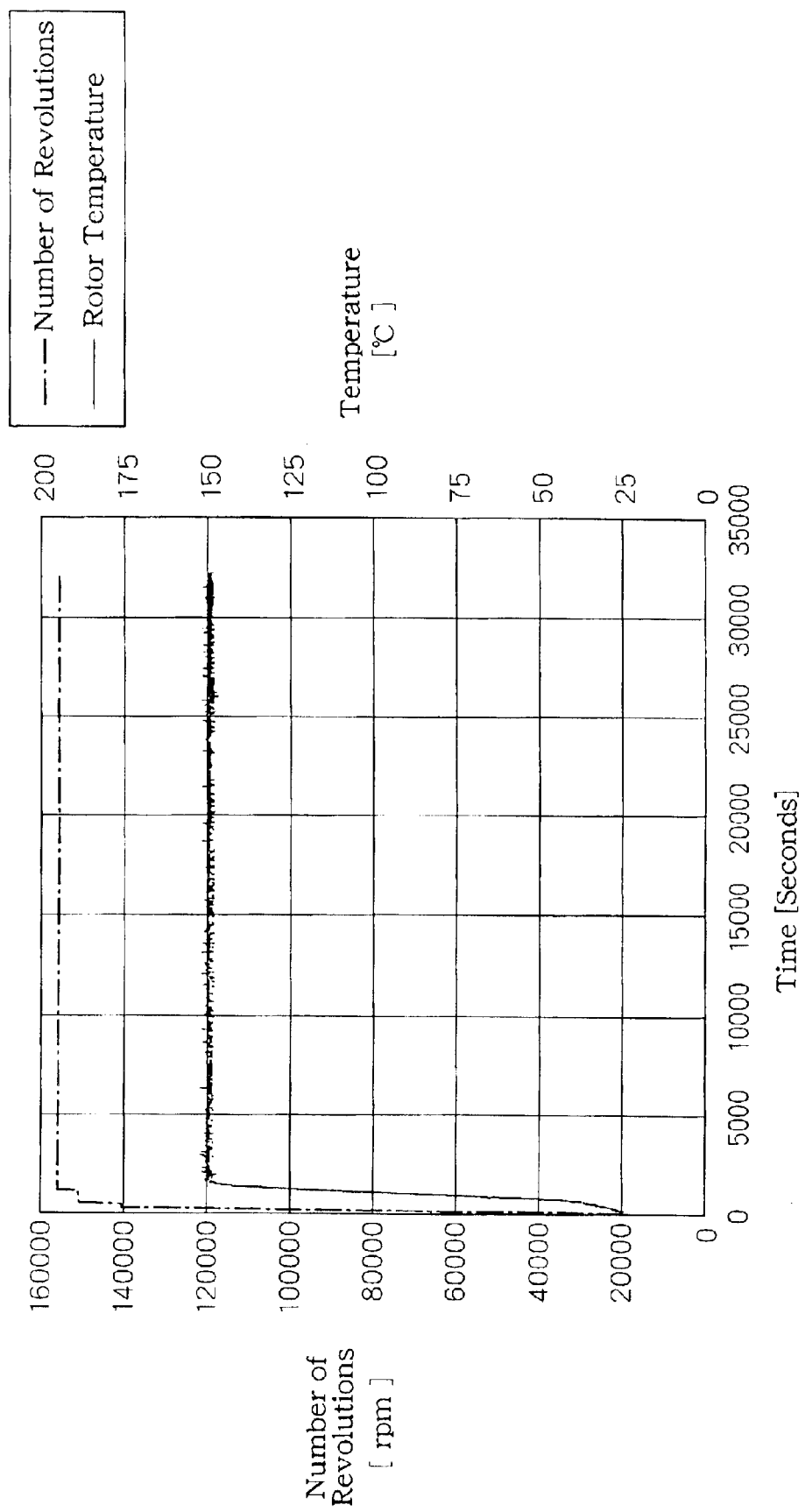
FIG. 7 is a figure showing the result of a test on the number of revolutions and temperature control using the apparatus according to the first embodiment.

FIG. 7 is a figure showing the result of a rotation test in which the rotor 1 made of titanium alloy (Ti-6A1-4V) was heated under the condition where the atmosphere surrounding the rotor 1 was at 200° C. and decompressed. In the test, the rotor 1 was rotated at 155,000 rpm and the number of revolutions was maintained for 100 hours. Then, the number of revolutions (a dotted chain line) and the temperature of the rotor 1 (a solid line) at this time were measured. The horizontal axis represents the time (seconds) and the vertical axis represents the number of revolutions (rpm) and the temperature (° C.) The temperature control was performed by PID control. As can be seen from the figure, it is clear that, while keeping a predetermined rotating speed, the temperature of the rotor 1 can be controlled at the same time. Also, it is clear that the control can be achieved with high precision. The high gravitational acceleration field at the maximum diameter of the test object was 738,809 g.

As described, the high-speed rotation testing apparatus according to the first embodiment can achieve high-speed rotation of the rotor 1 to which the test object is stored. Specifically, it can rotate the rotor 1 at a rotating speed of 600 m/s or more. Thereby, a high gravitational acceleration field of 1,000,000 g or more can be generated and the test object can be processed in the high gravitational field. Further, it is possible to maintain the high-speed rotation for a long time. Thus, the test object can be processed in the high gravitational field for a long time. Furthermore, since the rotor 1 can be heated by the radiation heat at the time of high-speed rotation, the temperature of the test object can be set to be processed in the high gravitational field. Specifically, it is possible to be heated at 400° C. or more.
(Second Embodiment)

Figure 8:
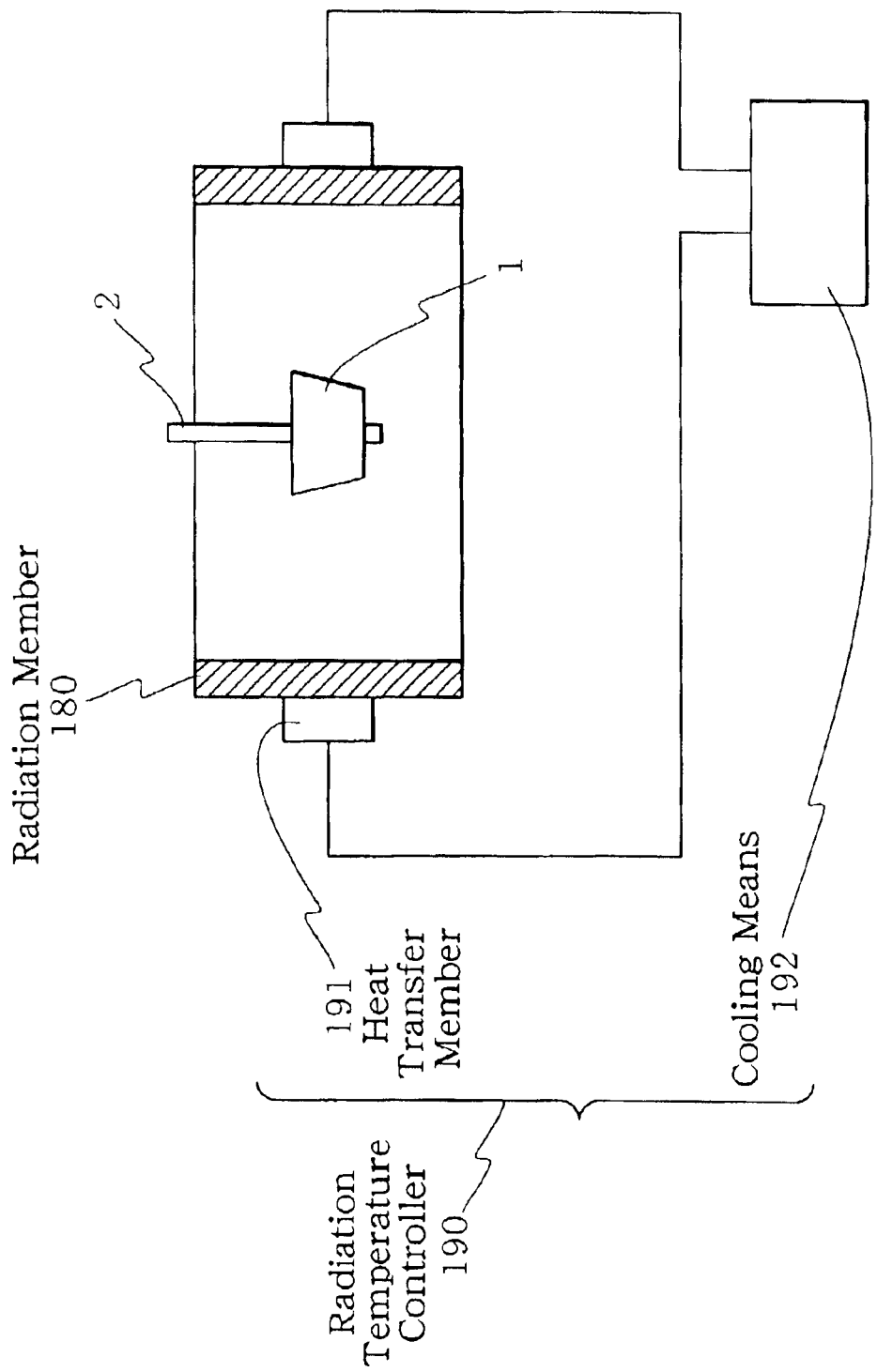
FIG. 8 is a schematic view showing a part of the configuration according to a second embodiment.
Figure 9:
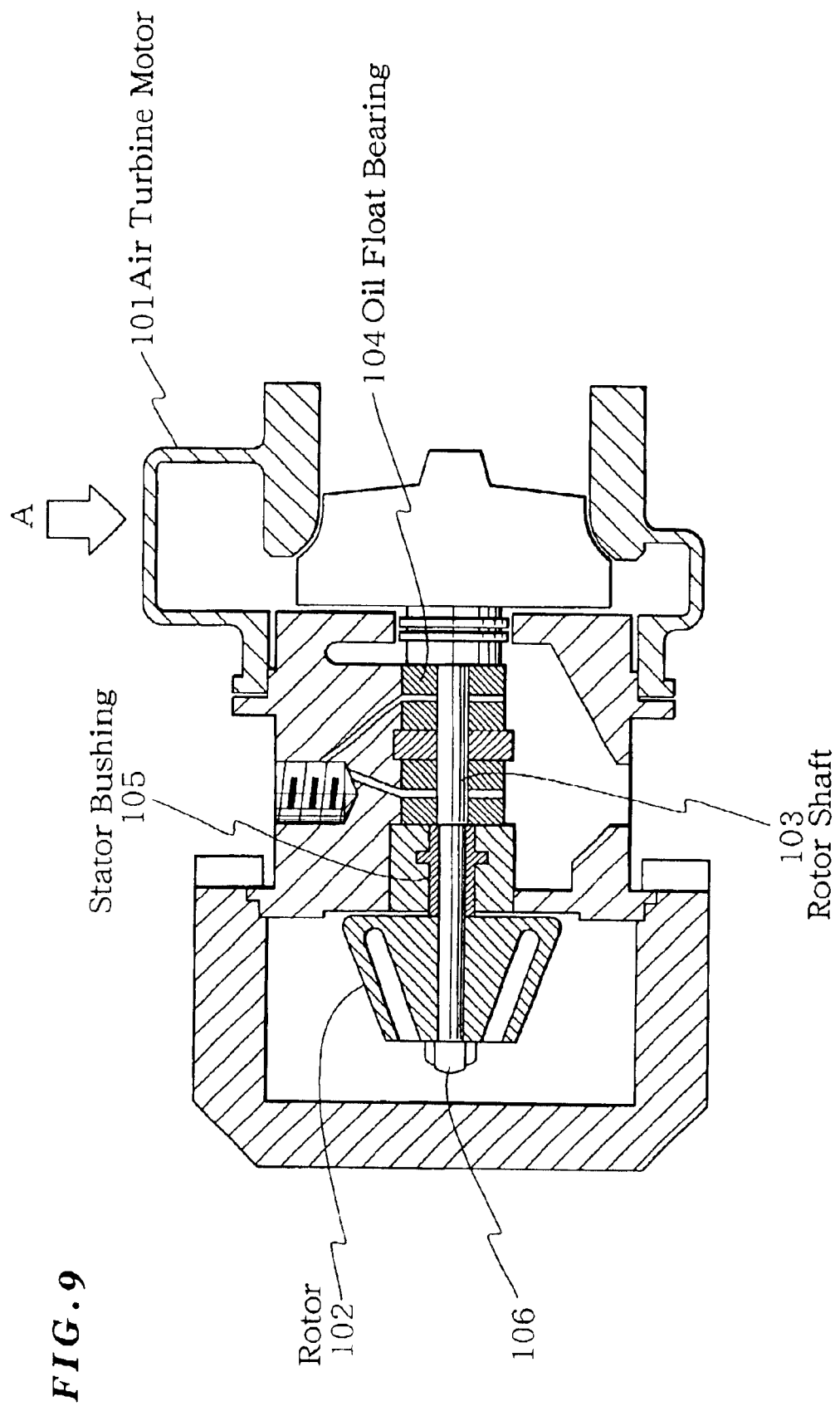
FIG. 9 is a cross section showing the configuration of a high-speed rotation testing apparatus of the related art.
Figure 10A:
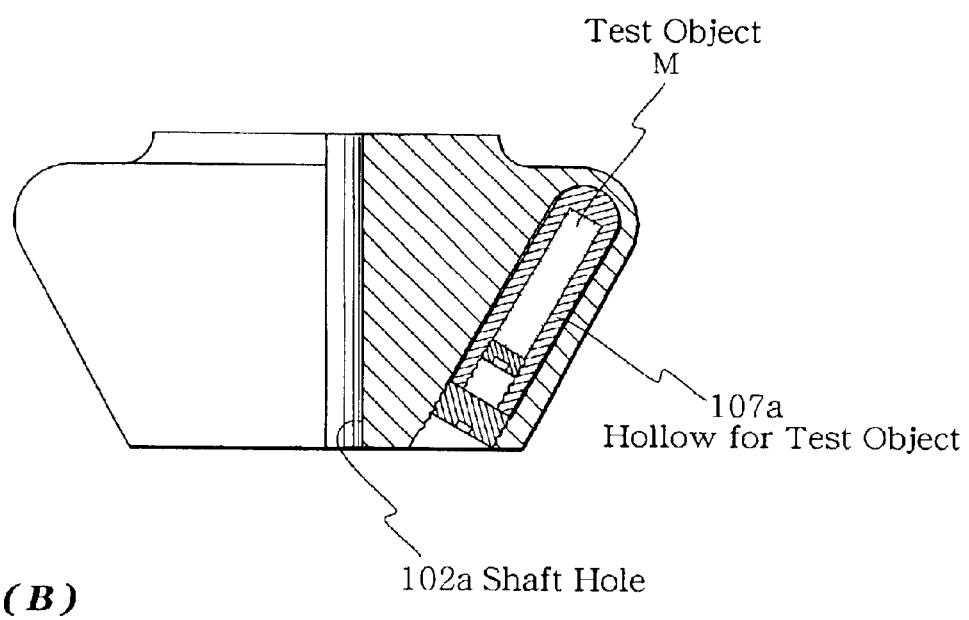
Figure 10B:
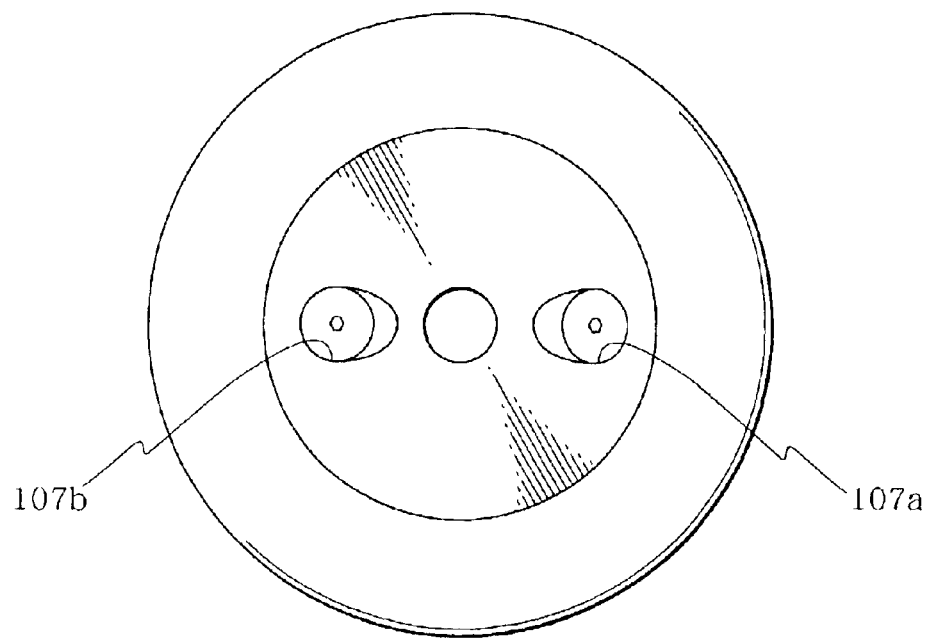
FIG. 10B shows the view of the rotor from the bottom.

Next, a second embodiment of the present invention will be described by referring to FIG. 8. In the embodiment, the configuration is substantially the same as that of the first embodiment. However, it differs from the first embodiment at a point that the radiation temperature controller 9 in the first embodiment for heating the radiation member 8 is, in the second embodiment, a means 190 for cooling a radiation member 180. Specifically, the radiation temperature controller 190 is composed of a heat transfer member 191 attached to the radiation member 180 and a cooling means 192 for cooling the heat transfer member 191. At this time, it is desirable that the radiation member be made of copper and the cooling means 192 be a device for cooling the heat transfer member by helium cooling. However, it is not limited to these.

As described, by the heat transfer member 191 cooled by the cooling means 192, the radiation member 180 is cooled. Then, through the radiation cooling by the radiation member 180, the rotor 1 can be cooled and the temperature of the rotor 1 can be decreased. As a result, the processing can be achieved in the high gravitational field while cooling the test object inside the rotor 1. In the experiment, it was possible to cool it to −20° C. or less.

The present invention is formed and functions as described. In the invention, the bushing for supporting the spindle is supported by the bushing supporting member without fixing so that the bushing becomes rotatable in the same direction as the rotating direction of the spindle. Thus, the friction between the spindle and the bushing is decreased so that seizure can be avoided. As a result, the invention can exhibit excellent effects such as achieving more high-speed rotation of the rotor and maintaining the high-speed rotation for a long time, which are not of the related art.

Also, in the case where the radiation member is provided surrounding the rotor, the rotor can be heated/cooled by the radiation. Therefore, in this case, the temperature of the rotor can be controlled even in a vacuum. Thus, a high-speed rotation can be achieved by suppressing the air resistance at the time of rotation through decompressing the atmosphere surrounding the rotor. Further, while processing the test object in the high gravitation field, the processing temperature can be controlled. Consequently, it becomes possible to set various processing conditions.

Furthermore, in the case where a torque applying device driven by the compressed air is used as a driving source of the rotor, generation of the heat from the driving source can be suppressed and the rotor can be prevented from being heated by the heat. Thereby, it becomes easier to control the temperature of the rotor, that is, the temperature of the test object.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2001-301480 (Filed on Sep. 28, 2001) including specification, claims, drawings and summary are incorporated herein by reference in its entirety.

What is claimed is:

1. A high-speed rotation testing apparatus, comprising:
   a rotor having a hollow for a test object for storing a predetermined test object;
   a spindle having one end portion connected to a rotation center of said rotor;
   a torque applicator connected to another end portion of said spindle to apply a predetermined torque to said spindle; and
   a casing for storing said rotor by sealing,
   wherein said casing comprises a decompressor that decompresses atmospheric pressure inside said casing and a holder that holds said spindle by inserting through of said spindle,
   wherein said holder comprises a bushing for supporting said spindle and a bushing supporting member that supports said bushing by inserting therethrough,
   wherein an inner diameter of said bushing supporting member is formed larger than an outer diameter of said bushing to be inserted into said bushing supporting member so that said bushing supporting member supports said bushing to be rotatable.

2. The high-speed rotation testing apparatus according to claim 1, wherein said bushing which is rotatably supported by said bushing supporting member is provided only on said torque applicator side of said holder.

3. The high-speed rotation testing apparatus according to claim 1, wherein, in a rotation center of said rotor, a spindle connecting portion projected from said rotor towards said torque applicator side is formed for connection to said spindle.

4. The high-speed rotation testing apparatus according to claim 3, wherein, in the projected end of said spindle connecting portion, a shaft hole for inserting and connecting said spindle is formed while providing a depth of the shaft hole not to penetrate said spindle connecting portion.

5. The high-speed rotation testing apparatus according to claim 1, wherein the torque applicator is an air turbine which is rotationally driven by a supply of compressed air.

6. The high-speed rotation testing apparatus according to claim 1, wherein said torque applicator is an electric driving motor.

7. The high-speed rotation testing apparatus according to claim 1, wherein, in the vicinity of said rotor inside said casing, a radiation member with a predetermined area is provided and wherein a radiation temperature controller that controls temperatures of said radiation member is provided.

8. The high-speed rotation testing apparatus according to claim 7, wherein said radiation member is formed in an annular shape so as to surround a rotation periphery of said rotor.

9. A high speed rotation testing apparatus comprising:
   a spindle; and
   a holder that rotatably holds the spindle,
   wherein said holder comprises:
   a casing having a storage chamber through which a lubricant flows;
   a housing with a cylindrical surrounding wall arranged in the storage chamber;
   a bushing supporting member supported by the housing; and
   a bushing which is rotatably supported by the bushing supporting member and into which the spindle is inserted,
   wherein oil films are formed between the casing and the cylindrical surrounding wall of the housing, between the bushing supporting member and the bushing, and between the spindle and the bushing, respectively.

10. The high-speed rotation testing apparatus according to claim 9, wherein the housing is supported by the casing while being urged in an axial direction of the spindle.

11. The high-speed rotation testing apparatus according to claim 10, wherein the housing is urged by a thrust spring.

12. The high-speed rotation testing apparatus according to claim 9, wherein the spindle is connected to a rotor having a hollow for a test object for storing a predetermined test object, and the rotor is stored in a sealed space and a torque is applied thereto.

13. The high-speed rotation testing apparatus according to claim 12, wherein, in a rotation center of the rotor, a spindle connecting portion is formed for connection to the spindle.

14. The high-speed rotation testing apparatus according to claim 13, wherein, in a projected end of the spindle connecting portion, a shaft hole for inserting and connecting said spindle is formed while providing a depth of the shaft hole not to penetrate the spindle connecting portion.

15. The high-speed rotation testing apparatus according to claim 12, wherein, in the vicinity of said rotor inside said sealed space, a radiation member with a predetermined area is provided and wherein a radiation temperature controller that controls temperatures of said radiation member is provided.

16. The high-speed rotation testing apparatus according to claim 15, wherein said radiation member is formed in an annular shape so as to surround a rotation periphery of said rotor.

* * * * *